United States Patent [19]

Smigel

[11] Patent Number: 4,690,776
[45] Date of Patent: Sep. 1, 1987

[54] METHOD OF MANUFACTURE OF A TOOTHPASTE COMPOSITION

[76] Inventor: Irwin E. Smigel, 635 Madison Ave., New York, N.Y. 10022

[21] Appl. No.: 817,043

[22] Filed: Jan. 8, 1986

Related U.S. Application Data

[62] Division of Ser. No. 706,001, Feb. 27, 1985, Pat. No. 4,603,045.

[51] Int. Cl.$^4$ .......................... A61K 7/18; B01J 13/00
[52] U.S. Cl. .................................. 252/315.3; 424/44; 424/49; 424/53; 424/57; 514/835
[58] Field of Search ...................... 424/49, 53, 57, 44; 514/835; 252/315.3

[56] References Cited

U.S. PATENT DOCUMENTS

| | | | |
|---|---|---|---|
| 2,751,328 | 6/1956 | Sanders | 252/315.3 X |
| 4,029,760 | 6/1977 | Holtzhauer et al. | 252/315.3 X |
| 4,066,745 | 1/1978 | Tomlinson et al. | 424/44 |
| 4,353,890 | 10/1982 | Scott | 252/315.3 X |
| 4,405,599 | 9/1983 | Smigel | 424/49 X |
| 4,603,045 | 7/1986 | Smigel | 424/52 |

Primary Examiner—Richard D. Lovering
Attorney, Agent, or Firm—Roberts, Spiecens & Cohen

[57] ABSTRACT

A method of preparing a toothpaste composition by the steps of adding calcium phosphate in an amount of 0.5 to 5% by weight of the composition and sodium perborate in an amount of 0.5 to 5% by weight of the composition to hot water to form a first mixture and agitating the first mixture, adding to the first mixture sorbitol in an amount of 1 to 50% by weight of the composition, cornstarch in an amount of 0.5 to 10% by weight of the composition and aluminum hydroxide in an amount of 0.01 to 1% by weight of the composition to form a second mixture and agitating the second mixture, adding to the second mixture dicalcium phosphate in an amount of 1 to 50% by weight of the composition and sodium monofluoride phosphate in an amount of 0.7 to 0.8% by weight of the composition to form a third mixture and agitating the third mixture, adding to the third mixture sodium bicarbonate, in an amount of 1 to 50% by weight of the composition, gradually adding increments of a flavoring material in an amount of 0.05 to 2% to control any foaming and to facilitate release of gases to form a fourth mixture, and adding to the fourth mixture sodium lauryl sulfoacetate in an amount of 0.1 to 5% and gum in an amount of 0.5 to 5% and agitating the fourth mixture until a homogeneous paste composition is obtained.

7 Claims, No Drawings

METHOD OF MANUFACTURE OF A TOOTHPASTE COMPOSITION

This is a division of application Ser. No. 706,001 filed Feb. 27, 1985, now U.S. Pat. No. 4,603,045.

FIELD OF THE INVENTION

The invention relates to a toothpaste composition and its method of preparation particularly where such composition is adapted not only for cleaning natural teeth, but composite filling material as well and which contains substances for preventing tooth decay.

BACKGROUND

In filling cavities from which dental caries have been removed, it has become an increasing practice to employ composite filling material which is similar in color to that of natural tooth material.

Such composite filling material is generally composed of a resinous substance which is polymerized in situ and which provides a hard bearing surface which has the natural appearance of a normal tooth.

Unfortunately, the composite filling material has inherent porosity and is relatively easily stained.

In a normal mouth, a salivary protein pellicle envelopes the tooth and is subject to plaque accumulation. Oral hygiene dictates the removal of the plaque accumulation in order to prevent decay of the tooth structure as well as serious diseases of the gums.

In my earlier U.S. Pat. No. 4,405,599, I disclosed toothpaste composition which is adapted for cleaning natural teeth and composite filling material as well.

SUMMARY OF THE INVENTION

An object of the invention is to provide a toothpaste which is adapted for cleaning natural teeth as well as bonded composite filling material which contains substances for preventing tooth decay.

A further object of the invention is to provide a toothpaste which is specifically addressed to the removal of stain from composite filling material as well as from the tooth itself which contains substances for preventing tooth decay.

Another object of the invention is to provide a toothpaste composition which will be effective to remove the protein pellicles which normally envelope the teeth as well as plaque accumulation and which contains substances for preventing tooth decay.

Another object of the invention is to provide a method for manufacture of the aforesaid tooth paste composition of the invention.

In order to satisfy the above and further objects of the invention, there is provided a toothpaste according to the invention consisting essentially of the following ingredients in percent, by weight:

| | |
|---|---|
| Dicalcium Phosphate, dihydrous | From 1.0% to 50% |
| Calcium Carbonate | From 1.0% to 50% |
| Sodium Bicarbonate | From 1.0% to 50% |
| Magnesium Carbonate | From 1.0% to 25% |
| Sorbitol 70% | From 1.0% to 50% |
| Corn Starch | From 0.5% to 10% |
| Cellulose Gum | From 0.5% to 5.0% |
| Calcium Peroxide | From 0.5% to 5% |
| Sodium Perborate | From 0.5% to 5% |
| Lathanol LAL (Sodium Lauryl Sulfoacetate) | From 0.1% to 5% |
| Aluminum Hydroxide | From 0.01 to 1% |
| Saccharinate (Sodium Salt) | From 0.05% to 2% |
| Flavoring material | From 0.05% to 2% |
| Alkylparaben | From 0.05% to 1.0% |
| Sodium Monofluoride Phosphate | From 0.70% to 0.80% |
| Titanium Dioxide | From 0.1% to 10% |
| Deinonized Water | From 10% to 50% |

The flavoring material is preferably composed as follows by weight:

| | |
|---|---|
| Menthol crystals | 20% |
| Oil of spearmint NF | 20% |
| Terpeneless spearmint | 30% |
| Oil of peppermint | 20% |
| Oil of anise | 10% |

In the ingredients which have been listed above for the toothpaste composition, there are ten active constituents which are present in a carefully balanced combination to achieve the objects of the invention. These consist of Dicalcium Phosphate, Calcium Carbonate, Magnesium Carbonate, Sodium Bicarbonate, Sorbitol, Cornstarch, Cellulose Gum, Calcium Peroxide, Sodium Perborate and Lathanol LAL. The invention covers these ingredients as well as their obvious equivalents.

The dicalcium phosphate, calcium carbonate sodium bicarbonate and magnesium carbonate are cleaning agents. Additionally, the sodium bicarbonate is an alkalizer and foaming agent.

The Sorbitol is a humectant.

The cornstarch and cellulose gum are thickening agents.

The calcium peroxide and sodium perborate are oxidizing agents.

The Lathanol is a detergent.

The Aluminum Hydroxide is a PH adjuster and is present in an amount to provide the composition with a substantially neutral PH.

The Saccharinate and flavoring material are present as taste ingredients and can be varied according to the desired taste to be provided for the composition.

The Alkylparaben is a preservative and includes any of the various alkylparaben compositions (such as methylparaben, propylparaben) capable of acting as perservative.

The sodium monofluoride phosphate is an active agent which is compatible in the overall composition and provides topical fluoride for inhibiting tooth decay.

The titanium dioxide is a whitening agent.

The Deionized Water is present in an amount to confer a suitable wetness for the composition in accordance to the desired viscosity of the composition.

DESCRIPTION OF PREFERRED EMBODIMENTS

One of the most important advances in dentistry in the past twenty-five years has been the development of the composite (tooth colored) restoration. This has revolutionized the profession from an esthetic concept. This coupled with the evolution of light activation with its capability of controlling setting time and the dentist's ability to etch the enamel of teeth and thus bond the composite material directly onto the tooth is known as bonding. Bonding enables the dentist to close spaces between teeth, repair chips in teeth, cover discolorations and reshape abnormally shaped teeth. This coupled with the imminent development of composites for chewing surfaces of posterior teeth is expected to make the composite filling material the overwhelming material of choice in dentistry. However, the composite material for all of its advantages is inherently porous and is subject to staining. There are two types of composite filling material:

A. The conventional material which is composed of 76% inorganic filler material, such as quartz or Barium glass and 24% Resin Matrix, such as BIS GMA which is the reactive product of BIS Phenol A and Glycidyl Methyl acrylic.

B. Microfill—composed of 35-55% inorganic filler—such as fumed silica and 45-65% Resin Matrix, generally BIS GMA.

The present invention provides for a toothpaste composition which is capable of cleaning natural teeth as well as the composite filling material.

The invention provides a toothpaste composition which will satisfy the above and which has a specific balance of active ingredients to clean natural teeth as well as composite filling material. This composition consists of the following ingredients, given in percent by weight.

| INGREDIENT | AMOUNT IN % |
|---|---|
| Dicalcium Phosphate | 7.5 |
| Calcium Carbonate | 5 |
| Sodium Bicarbonate | 5 |
| Magnesium Carbonate | 1.25 |
| Sorbitol 70% | 20 |
| Cornstarch | 1.3 |
| Cellulose Gum | 4.0 |
| Calcium Peroxide | 2.4 |
| Sodium Perborate | 1.5 |
| Lathonol LAL (Sodium Lauryl Sulfoacetate) | 0.7 |
| Aluminum Hydroxide | 0.1 |
| Saccharinate (Sodium Salt) | 0.5 |
| Flavoring Material | 1 |
| Consisting of: | |
| Menthol crystals 20% | |
| 0.1 of Spearmint NF 20% | |
| Terpeneless Spearmint 30% | |
| Oil of Peppermint 20% | |
| Oil of Anise (imitation) 10% | |
| Methylparaben | 0.5 |
| (Hydroxybenzoic acid methyl ester) | |
| Propylparaben | 0.03 |
| (Hydroxybenzoic acid propylester) | |
| Sodium Monofluoride Phosphate | 0.76 |
| Titanium Dioxide | 1.0 |
| Deionized Water (to make up 100%) | 47.46 |

The above composition had the paste-like texture of standard toothpaste and was found to be exceptionally effective in its ability to remove stains and plaque from normal teeth as well as composite filling material. The sodium monofluoride phosphate is compatible with the remainder of the ingredients and is active to provide a topical fluoride composition on the teeth and the composite filling material to inhibit decay.

It has been found that in order to prepare the toothpaste composition and retain the activity of the sodium monofluoride phosphate, the composition must be prepared as set forth in the following example.

EXAMPLE

The required amount of water was heated to 150° F. and was added to a Hobart mixer whose agitation means was activated.

The calcium peroxide and sodium perborate were added to the hot water and agitation was continued for ten minutes.

The sorbitol, methylparaben (or propylparaben or mixtures thereof), cornstarch and aluminum hydroxide were then added and agitation was continued for an additional ten minutes.

Thereafter the dicalcium phosphate, calcium carbonate, magnesium carbonate and sodium monofluoride phosphate were added and agitation was continued for another ten minutes.

Thereafter the sodium bicarbonate was added gradually and if there is any foaming which takes place and persists, increments of the flavoring material are added to control the foam and facilitate the release of gases.

The titanium dioxide and saccharinate were then added and agitation was continued for at least half an hour.

Finally, the Lathonol and the cellulose gum were added and agitation was continued until a homogeneous mass was obtained.

It was found that the homogeneous mass was of suitable paste-like composition for use as the toothpaste composition of the invention.

While the invention has been described in connection with specific embodiments thereof, it will become apparent to those skilled in the art that various equivalents may be used within the scope and spirit of the invention as defined by the attached claims.

What is claimed is:

1. A method of preparing a toothpaste composition comprising adding calcium phosphate in an amount of 0.5 to 5% by weight of the composition and sodium perborate in an amount of 0.5 to 5% by weight of the composition to hot water to form a first mixture and agitating the first mixture, adding to said first mixture sorbitol in an amount of 1 to 50% by weight of the composition, cornstarch in an amount of 0.5 to 10% by weight of the composition and aluminum hydroxide in an amount of 0.01 to 1% by weight of the composition to form a second mixture and agitating the second mixture, adding to said second mixture dicalcium phosphate in an amount of 1 to 50% by weight of the composition and sodium monofluoride phosphate in an amount of 0.7 to 0.8% by weight of the composition to form a third mixture and agitating the third mixture, adding to the third mixture sodium bicarbonate, in an amount of 1 to 50% by weight of the composition, gradually adding increments of a flavoring material in an amount of 0.05 to 2% to control any foaming and to facilitate release of gases to form a fourth mixture, and adding to the fourth mixture sodium lauryl sulfoacetate in an amount of 0.1 to 5% and gum in an amount of 0.5 to 5% and agitating the fourth mixture until a homogeneous paste composition is obtained.

2. A method as claimed in claim 1 wherein the water is initially heated to 150° F.

3. A method as claimed in claim 2 wherein the first, second and third mixtures are each agitated for ten minutes.

4. A method as claimed in claim 2 comprising adding an alkylparaben in an amount of 0.05 to 1.0% by weight of the composition to the second mixture before agitation thereof.

5. A method as claimed in claim 2 comprising adding calcium carbonate in an amount of 1 to 50% by weight of the composition and magnesium carbonate in an amount of 1 to 25% by weight of the composition to the third mixture before agitation thereof.

6. A method as claimed in claim 2 comprising adding to the fourth mixture titanium dioxide as a whitening agent in an amount of 0.1 to 10% by weight of the composition and saccharinate in an amount of from 0.05 to 2% by weight of the composition and the resulting mixture is agitated for at least one half hour.

7. A method as claimed in claim 2 comprising adding a cellulose gum in an amount of 0.5 to 5% by weight of the composition to the fourth mixture before agitation thereof.

* * * * *